United States Patent
Liao et al.

(10) Patent No.: US 11,873,278 B2
(45) Date of Patent: Jan. 16, 2024

(54) METHOD FOR PREPARING LOW MIGRATION PLASTICIZER OF DI-2-ETHYLHEXYL TEREPHTHALATE

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Hsun-Min Lin, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 123 days.

(21) Appl. No.: 17/398,003

(22) Filed: Aug. 10, 2021

(65) Prior Publication Data
US 2022/0242813 A1 Aug. 4, 2022

(30) Foreign Application Priority Data
Jan. 29, 2021 (TW) ................... 110103452

(51) Int. Cl.
*C07C 67/08* (2006.01)
*C08K 5/12* (2006.01)

(52) U.S. Cl.
CPC .............. *C07C 67/08* (2013.01); *C08K 5/12* (2013.01)

(58) Field of Classification Search
CPC .......... C07C 67/08; C07C 69/82; C08K 5/12; C08K 5/0016; C08L 27/06
See application file for complete search history.

(56) References Cited

FOREIGN PATENT DOCUMENTS

| | | | |
|---|---|---|---|
| CN | 105001091 A | | 10/2015 |
| CN | 108640837 A | | 10/2018 |
| CN | 109081780 A | | 12/2018 |
| CN | 111960943 | * | 11/2020 |
| CN | 111960943 A | | 11/2020 |
| EP | 2781502 A1 | | 9/2014 |
| KR | 20190139022 | * | 12/2019 |
| TW | 200846315 A | | 12/2008 |
| TW | 201904927 A | | 2/2019 |
| TW | 201932444 A | | 8/2019 |
| WO | WO2018167718 A1 | | 9/2018 |

OTHER PUBLICATIONS

Organic Chemistry (two pages, Published 2013) (Year: 2013).*
KR20190139022 translation (Year: 2019).*
CN111960943 translation (Year: 2020).*

* cited by examiner

*Primary Examiner* — Yevgeny Valenrod
*Assistant Examiner* — Blaine G Doletski
(74) *Attorney, Agent, or Firm* — Li & Cai Intellectual Property Office

(57) ABSTRACT

A method for preparing a low migration plasticizer of di-2-ethylhexyl terephthalate is provided. The method includes a step of adding a short chain alcohol component having 4 to 6 carbon atoms and a long chain alcohol component having 9 to 13 carbon atoms in an esterification reaction between terephthalic acid and 2-ethylhexanol, so as to obtain a modified di-2-ethylhexyl terephthalate including residues derived from the short chain alcohol component and the long chain alcohol component. The esterification reaction is carried out under a temperature from 30° C. to 225° C. and a pressure from 80 mbar to 1033 mbar.

10 Claims, 1 Drawing Sheet

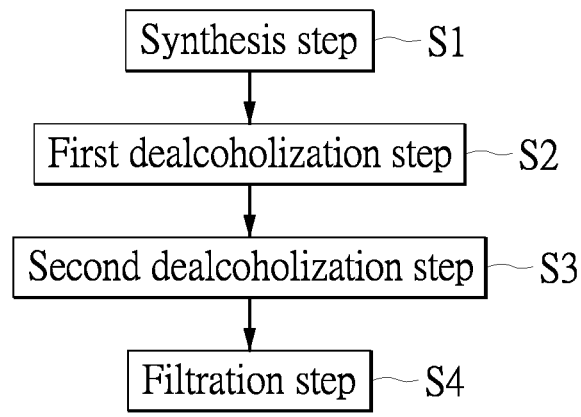

METHOD FOR PREPARING LOW MIGRATION PLASTICIZER OF DI-2-ETHYLHEXYL TEREPHTHALATE

CROSS-REFERENCE TO RELATED PATENT APPLICATION

This application claims the benefit of priority to Taiwan Patent Application No. 110103452, filed on Jan. 29, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for preparing di-2-ethylhexyl terephthalate, and more particularly to a method for preparing a low migration plasticizer of di-2-ethylhexyl terephthalate. A resulting di-2-ethylhexyl terephthalate that has low migration can serve as a low migration environmentally friendly plasticizer for polyvinyl chloride (PVC) products.

BACKGROUND OF THE DISCLOSURE

Plasticizer is a common additive used in the polymer industry, and has been widely used in the processing of plastics and rubbers for increasing their plasticity and processability to allow products to have excellent softness, elasticity, and toughness. DOTP (di-2-ethylhexyl terephthalate) is a non-toxic, environmentally friendly and non-phthalate plasticizer, and is commonly used in the formation process of polyvinyl chloride (PVC) to allow the PVC to be easily processed. However, DOTP has poor compatibility with PVC, and is thus easily released to a surface of a product (precipitation phenomenon), which affects the appearance and hand feel of the PVC.

A solution in the related art is to add an additional component into a PVC material (e.g., citrate), so as to inhibit the migration of DOTP through the interaction between the additional component and DOTP, thereby improving the precipitation phenomenon of a PVC product. However, the addition of the additional component may cause an increase in costs. Another solution in the related art is to apply an acrylic layer onto a surface of a product. Although the acrylic layer can inhibit the migration of DOTP, so as to achieve and improve the precipitation phenomenon of the PVC product, such a solution may cause an increase in costs and process complexity.

SUMMARY OF THE DISCLOSURE

In response to the above-referenced technical inadequacies, the present disclosure provides a method for preparing a low migration plasticizer of di-2-ethylhexyl terephthalate. The resulting di-2-ethylhexyl terephthalate has low migration and good processability, and can serve as an environmentally friendly plasticizer.

In one aspect, the present disclosure provides a method for preparing a low migration plasticizer of di-2-ethylhexyl terephthalate. The method includes a synthesis step of adding at least one short chain alcohol component having 4 to 6 carbon atoms and at least one long chain alcohol component having 9 to 13 carbon atoms in an esterification reaction between terephthalic acid and 2-ethylhexanol, so as to obtain a crude ester product. The synthesis step is carried out under a temperature from 30° C. to 225° C. and a pressure from 80 mbar to 1033 mbar.

In one embodiment of the present disclosure, in the synthesis step, an equivalent amount of the 2-ethylhexanol is 2 to 5 times an equivalent amount of the terephthalic acid.

In one embodiment of the present disclosure, an added amount of the at least one short chain alcohol component having 4 to 6 carbon atoms is from 0.1% to 0.5% of the equivalent amount of the terephthalic acid, and an added amount of the at least one long chain alcohol component having 9 to 13 carbon atoms is from 0.1% to 0.5% of the equivalent amount of the terephthalic acid.

In one embodiment of the present disclosure, in the synthesis step, the terephthalic acid is used in the same amount as the 2-ethylhexanol to carry out the esterification reaction, the at least one short chain alcohol component having 4 to 6 carbon atoms and the at least one long chain alcohol component having 9 to 13 carbon atoms are added to modify the di-2-ethylhexyl terephthalate, and an excess amount of the 2-ethylhexanol is added to continue the esterification reaction.

In one embodiment of the present disclosure, the esterification reaction is ended when an acid value is less than 0.07 mg KOH/g.

In one embodiment of the present disclosure, the method for preparing the low migration plasticizer of di-2-ethylhexyl terephthalate further includes a first dealcoholization step of preliminarily reducing an alcohol content of the crude ester product under a temperature from 180° C. to 200° C. and a pressure from 80 mbar to 500 mbar.

In one embodiment of the present disclosure, after the first dealcoholization step, the method for preparing the low migration plasticizer of di-2-ethylhexyl terephthalate further includes a second dealcoholization step of further reducing the alcohol content of the crude ester product by gas stripping.

In one embodiment of the present disclosure, the method for preparing the low migration plasticizer of di-2-ethylhexyl terephthalate further includes a filtration step of filtering out at least the catalyst.

In one embodiment of the present disclosure, the low migration plasticizer of di-2-ethylhexyl terephthalate has a molecular weight from 334 to 460, not including the molecular weight of 390, a color number of less than 20 APHA, and a water content of less than 0.05%.

In one embodiment of the present disclosure, the low migration plasticizer of di-2-ethylhexyl terephthalate has a structure represented by formula (1):

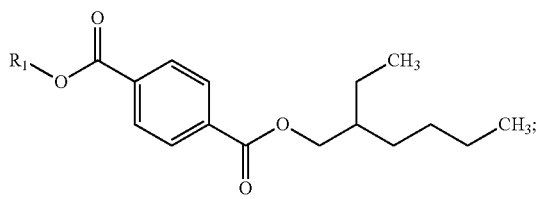

formula (1)

$R_1$ represents an alkyl group having 4 to 13 carbon atoms, not including the alkyl group having 8 carbon atoms.

One of the beneficial effects of the subject matter provided by the present disclosure is that, by virtue of "adding at least one short chain alcohol component having 4 to 6 carbon atoms and at least one long chain alcohol component having 9 to 13 carbon atoms in an esterification reaction between terephthalic acid and 2-ethylhexanol", a low migration plasticizer of di-2-ethylhexyl terephtalate with high purity and low APHA color number can be obtained, and is not easily released to a surface of an applied plastic product when added in a higher amount.

Furthermore, the low migration plasticizer of di-2-ethylhexyl terephthalate prepared by the method of the present disclosure has very good compatibility with polyvinyl chloride (PVC), and is suitable to be used together with the PVC in a higher amount (i.e., 80 PHR or more), so as to produce PVC products. In use, the low migration plasticizer of di-2-ethylhexyl terephthalate has good processability and can simplify a production process and reduce costs.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawing, in which:

The FIGURE is a flowchart of a method for preparing a low migration plasticizer of di-2-ethylhexyl terephthalate of the present disclosure.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

PVC materials have a wide range of uses, including soft plastic products (e.g., food packages and medical equipment), hard plastic products (e.g., pipe materials), and other products (e.g., adhesives, insulating cladding materials, surface materials, and lining materials). A plasticizer is able to allow the PVC materials to have an excellent softness, elasticity, and toughness. Therefore, the present disclosure provides a method for preparing a low migration plasticizer of di-2-ethylhexyl terephthalate. The resulting low migration plasticizer of di-2-ethylhexyl terephthalate not only has good compatibility with polyvinyl chloride (PVC), but also has low migratability, and does not easily migrate when added in a higher amount and thus does not affect an appearance and hand feel of a processed good or product.

Referring The FIGURE, the method for preparing the low migration plasticizer of di-2-ethylhexyl terephthalate of the present disclosure according to an embodiment at least includes: step S1, a synthesis step; step S2, a first dealcoholization step; step S3, a second dealcoholization step; and step S4, a filtration step.

The synthesis step includes, in an esterification reaction between terephthalic acid and 2-ethylhexanol, adding at least one short chain alcohol component having 4 to 6 carbon atoms and at least one long chain alcohol component having 9 to 13 carbon atoms to graft modify a resulting low migration composite plasticizer of di-2-ethylhexyl terephthalate. In the synthesis step, the at least one short chain alcohol component and the at least one long chain alcohol component are grafted onto molecular chains of the di-2-ethylhexyl terephthalate. In consideration of reaction efficiency and economic aspects, an equivalent amount of the 2-ethylhexanol is 2 to 5 times an equivalent amount of the terephthalic acid. A reaction temperature is 30° C. to 230° C., and preferably 30° C. to 225° C. A reaction pressure is 50 mbar to 1033 mbar, and preferably 80 mbar to 1033 mbar. As used herein, the term "grafted" means that the at least one short chain alcohol component and the at least one long chain alcohol component are covalently bonded to the molecular chains of the di-2-ethylhexyl terephthalate.

In the embodiment of the present disclosure, the esterification reaction is carried out in the presence of a catalyst. Preferably, the catalyst is a tin-based or titanium-based catalyst, and an added amount thereof is 0.2% to 1% of a weight of the terephthalic acid. If the added amount of the catalyst is less than 0.2% of the weight of the terephthalic acid, the esterification reaction cannot be effectively promoted and a reaction rate thereof cannot be increased. If the added amount of the catalyst is greater than 1% of the weight of the terephthalic acid, a promotion effect on the esterification reaction is ineffective and uneconomical, and a resulting product may even exhibit coloration. The tin-based catalyst may be an organotin compound, specific examples of which include: dibutyltin diacetate, dibutyltin laurate, tributyltin oxide, dibutyltin oxide, and monobutyltin oxide. The titanium-based catalyst may be an organotitanium compound, specific examples of which include: titanium tetraethoxide, titanium tetrapropoxide, titanium tetraisopropoxide, titanium tetra-n-butoxide, titanium tetraisobutoxide, titanium tetrahexoxide, titanium tetraoctoxide, titanium tetra-2-ethylhexoxide, tetraisopropyl titanate, tetra-n-butyl titanate, and other tetra-alkyl titanate compounds.

It is worth mentioning that, the at least one short chain alcohol component having 4 to 6 carbon atoms can assist in improving the compatibility of the di-2-ethylhexyl terephthalate with PVC. The at least one short chain alcohol component having 4 to 6 carbon atoms can have a linear or branched structure, and specific examples thereof include n-butanol and isobutanol. The at least one long chain alcohol component having 9 to 13 carbon atoms can assist in inhibiting the migration of the di-2-ethylhexyl terephthalate, so that the di-2-ethylhexyl terephthalate does not migrate easily in a plastic material (e.g., PVC), and is unlikely to release to a surface of an applied plastic product when added in a higher amount. The at least one long chain alcohol component having 9 to 13 carbon atoms can have a linear or branched structure, and specific examples thereof include 911 alcohol, 2-propylheptanol, and isodecyl alcohol. In the embodiment of the present disclosure, an added amount of the at least one short chain alcohol component having 4 to 6 carbon atoms is 0.1% to 0.5% of the equivalent amount of the terephthalic acid, and an added amount of the at least one long chain alcohol component having 9 to 13 carbon atoms is 0.1% to 0.5% of the equivalent amount of the terephthalic acid.

It is worth mentioning that, in the synthesis step, the terephthalic acid, the 2-ethylhexanol, the short chain alcohol component, and the long chain alcohol component are added in a specific order for reaction. More specifically, in the synthesis step, the terephthalic acid is used in the same amount as the 2-ethylhexanol to carry out the esterification reaction. After that, the short chain alcohol component and the long chain alcohol component are added to graft modify the resulting di-2-ethylhexyl terephthalate, and an excess amount of the 2-ethylhexanol is added to continue the esterification reaction. The esterification reaction is ended when an acid value is less than 0.07 mg KOH/g. The excess amount of the 2-ethylhexanol can not only act as a water removing agent to quickly remove water generated in a reaction, but also increase a reactant concentration to promote the reaction towards the formation of an ester.

After the completion of the synthesis step, a crude ester product is obtained and at least includes a low migration di-2-ethylhexyl terephthalate resulting from the reaction. The low migration di-2-ethylhexyl terephthalate can have a structure represented by formula (1) and a molecular weight from 334 to 460.

formula (1)

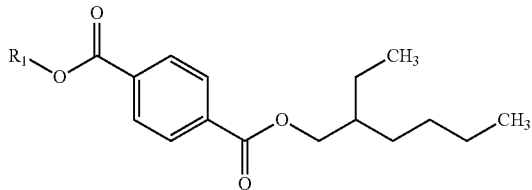

In formula (1), R1 represents an alkyl group having 4 to 13 carbon atoms, not including the alkyl group having 8 carbon atoms.

In order to increase purity and physical properties of the low migration di-2-ethylhexyl terephthalate, a first dealcoholization step, a neutralization step, a stripping step (also called "a second dealcoholization step"), and a filtration step are performed after the completion of the synthesis step. In the embodiment of the present disclosure, the first dealcoholization step includes preliminarily reducing a residual alcohol content of the crude ester product under a temperature from 180° C. to 200° C. and a pressure from 80 mbar to 500 mbar. The stripping step includes further reducing the residual alcohol content of the crude ester product to less than 300 ppm. The filtration step includes at least filtering out the catalyst and impurities in the crude ester product. After the completion of the first dealcoholization, stripping and filtration steps, a high quality ester plasticizer having a purity of greater than 99%, a color number of less than 20 APHA as defined in accordance with the ASTM D1209 standard, and a water content of less than 0.05% can be obtained.

The low migration di-2-ethylhexyl terephthalate prepared by the method of the present disclosure can be used together with a polyvinyl chloride resin to produce a polyvinyl chloride plastic product. As used herein, the term "polyvinyl chloride resin" refers to a homopolymer of polyvinyl chloride resin, a copolymer of polyvinyl chloride resin, or any mixture thereof. The copolymer of polyvinyl chloride resin is formed by copolymerizing vinyl chloride monomers with other monomers or monomer blends. Suitable monomers include: vinyl acetate, ethylene, propylene, maleate, methacrylate, acrylate, high alcohol vinyl ester, urethane, chlorinated urethane, and methyl methacrylate. Specific examples of the monomer blends include: ethylene-vinyl acetate copolymer, acrylonitrile-butadiene-styrene terpolymer, and acrylonitrile-butadiene copolymer.

It is worth mentioning that, the low migration di-2-ethylhexyl terephthalate has a long chain molecular structure, and thus has low migration ability. Furthermore, the low migration di-2-ethylhexyl terephthalate is more available for entanglement with polyvinyl chloride, and thus becomes difficult to be released or to migrate outwardly when added in a higher amount. In addition, the low migration di-2-ethylhexyl terephthalate has a purity of greater than 99.5%, a color number of less than 20 APHA, and a water content of less than 0.05%. Therefore, the resulting polyvinyl chloride plastic product can have high transparency, low degree of coloring, and a resistance to migration (i.e., a low migration ability).

One of the beneficial effects of the subject matter provided by the present disclosure is that, by virtue of "adding at least one short chain alcohol component having 4 to 6 carbon atoms and at least one long chain alcohol component having 9 to 13 carbon atoms in an esterification reaction between terephthalic acid and 2-ethylhexanol", a low migration plasticizer of di-2-ethylhexyl terephthalate with high purity and low APHA color number can be obtained, and is not easily released to a surface of an applied plastic product when added in a higher amount (i.e., 80 PHR or more).

Furthermore, the low migration plasticizer of di-2-ethylhexyl terephthalate prepared by the method of the present disclosure has very good compatibility with polyvinyl chloride (PVC), and is suitable to be used together with PVC in a higher amount, so as to produce PVC products. In use, the low migration plasticizer of di-2-ethylhexyl terephthalate has good processability and can simplify a production process and reduce costs.

PREPARATION EXAMPLE

A method for preparing a plasticizer of di-2-ethylhexyl terephthalate of the present disclosure includes the following steps:
1) A mixture of terephthalic acid (PTA) or its derivative, 2-ethylhexanol (2-EH), and 911 alcohol is used as a material, in which an equivalent molar ratio of the PTA or its derivative, the 2-EH, and the 911 alcohol is 1:2.2-3.8:0.029, and based on a total weight of the reactants (the PTA or its derivative and the 2-EH), an added amount of the PTA or its derivative is 23 wt % to 35 wt %, an added amount of the 2-EH is 65 wt % to 77 wt %, and an added amount of the 911 alcohol is 0.0014 wt %;

2) 0.1 wt % to 6 wt % of a metal-containing catalyst or an inorganic acid catalyst is added as an esterification catalyst based on a total amount of a low migration di-2-ethylhexyl terephthalate;

3) a one-step esterification reaction using the mixture of the PTA or its derivative, the 2-EH and the 911 alcohol obtained in step (1) is carried out under a pressure from 5 mbar to 1033 mbar and a temperature from 200° C. to 225° C., preferably under a pressure from 15 mbar to 950 mbar and a temperature from 220° C. to 240° C., and in the presence of the esterification catalyst obtained in step (2), which is over a period from 9 to 16 hours until an acid value of a reaction mixture is less than 1 mg KOH/g;

4) after the completion of the reaction, the reaction mixture is neutralized with an aqueous solution containing 5 wt % to 20 wt % of an alkali metal hydroxide to an acid value of less than 0.05 mg KOH/g, and is then reduced in alcohol content, dried and filtered so as to obtain a low migration plasticizer of DOTP ester.

The method for preparing the low migration plasticizer of di-2-ethylhexyl terephthalate of the present disclosure removes water generated in a reaction together with a reactant alcohol in an azeotropic manner that uses an azeotropic temperature from 90° C. to 180° C., in which the water generated in the reaction must be removed. When the acid value of the reaction mixture is less than 1 mg KOH/g, the reaction mixture in a reaction tank includes not only the low migration plasticizer of DOTP ester that is to be synthesized, but also a partially esterified dicarboxylic acid and an excess amount of the reactant alcohol and the catalyst.

The method for preparing the low migration plasticizer of di-2-ethylhexyl terephthalate of the present disclosure carries out a neutralization reaction that uses an aqueous solution containing an alkali metal hydroxide as a neutralizer to neutralize the residual acid of the esterification reaction after the completion of the esterification reaction, in which the residual acid is formed into a salt. A concentration of the neutralizer is 5 wt % to 25 wt %, preferably 9 wt % to 16 wt %, and an added amount of the neutralizer is 4 to 5 times the acid value of the reaction mixture. The alkali metal hydroxide of the aqueous solution is preferably sodium hydroxide. The salt obtained in the neutralization reaction can form into solid crystals in the manner of condensation and precipitation that can be easily removed by filtration in a subsequent process.

When the neutralization reaction proceeds to the reaction mixture reaching an acid value of less than 0.05 mg KOH/g, a distillation process is performed to reduce an alcohol content to less than 300 ppm, and to allow hydrolysis compounds of the catalyst to be easily removed by filtration. Furthermore, it is able to add a high surface area absorbent such as activated carbon to assist in the removal of the hydrolyzed catalyst.

Drying and filtration processes are performed after removing the excess amount of the reactant alcohol. In the drying process, an inert gas such as nitrogen or no inert gas is directed into the reaction tank. After that, a partially reacted carboxylic acid, hydrolysis products of the catalyst, and the absorbent can be removed by the filtration process that is performed under room temperature or a heating condition. Materials commonly used for filtration such as cellulose, diatomaceous earth, and sawdust powder can be used in the filtration process.

The method for preparing the low migration plasticizer of di-2-ethylhexyl terephthalate of the present disclosure performs filtration and purification processes under room temperature or 100° C. to remove a salt resulting from neutralization, a metal salt catalyst, and impurities, so as to obtain an ester product. Particularly, the ester product has a purity of greater than 99.5%, a color number of 10 APHA, and a resistance to migration, and can thus act as a plasticizer.

The low migration di-2-ethylhexyl terephthalate prepared by the method of the present disclosure is formed by grafting short chain alcohol and long chain alcohol components onto the conventional di-2-ethylhexyl terephthalate (DOTP), and does not contain phthalic acid as a material. The low migration di-2-ethylhexyl terephthalate, when used as a plasticizer, has a quality and processing physical properties equivalent to those of a phthalate acid based plasticizer such as DOP and DINP, and when applied to a plastic product, has a migration rate less than that of the conventional DOTP. Particularly, when the low migration di-2-ethylhexyl terephthalate of the present disclosure as a plasticizer is added in an amount reaching 80 PHR, the migration rate thereof is less than that of the conventional DOTP, thus being able to be applied to soft PVC products in a higher amount (i.e., 80 PHR or more), such as medical tubes, wires and cables, sports cushions, table mats, fitness balls, gloves, and shoe materials.

The following examples and comparative examples are provided below to demonstrate the effects of the present disclosure, but the scope of the present disclosure is not limited thereto.

Ester plasticizers prepared by esterification reaction processes as described in the following examples and comparative examples are measured for acid value (mg KOH/g), purity (%), APHA color number, and processing physical properties.

1. Acid value (mg KOH/g): measured in accordance with the ASTM D1045 standard.
2. Purity (%): measured by a gas chromatography method.
3. APHA color number: measured in Pt—Co color units.
4. Processing physical properties: tested through samples with Compositions (A) and (B):

Composition (A) includes 100 PHR of PVC, 40 PHR of a plasticizer, and 2 PHR of a barium-zinc stabilizer. Composition (B) includes 100 PHR of PVC, 80 PHR of the plasticizer, and 2 PHR of the barium-zinc stabilizer. The mixture of Composition (A) or (B), after being thoroughly mixed at 175° C., was processed for 5 minutes by a roller mill to form 0.4 mm sheet samples. The samples of Composition (A) were subsequently tested for processing physical properties including initial coloring degree, heat resistance, transparency, plastification coefficient, and tensile strength. In addition, the samples of Compositions (A) and (B) were each tested for migration rate.

a. Test of Initial Coloring Degree:

The 0.4 mm sheet sample of Composition (A) was preheated at 185° C. for 3 minutes and heated at 185° C. for 3 minutes by a pressure apparatus, and was then cooled for 3 minutes to form a 4 mm sheet sample, which was detected for yellowness index by a spectrophotometer (MS-020 PLUS).

b. Test of Heat Resistance:

The 0.4 mm sheet sample of Composition (A) was cut into a size of 25 cm×1.5 cm×0.2 cm and tested for heat resistance under conditions of 180° C. and 2 hours by an automatic testing oven (Metrastat® PSD 260).

c. Test of Migration Rate:

The 0.4 mm sheet samples of Compositions (A) and (B), after being cooled, were each cut into a size of 5 cm×5 cm and sequentially sandwiched between PVC rigid tapes and flat glass plates, the PVC rigid tapes each having a predetermined weight and a size of 5 cm×5 cm. The resulting combinations were each placed in an oven with a 3 kg load for a migration rate comparison under conditions of 180° C. and 2 hours.

A migration rate is calculated by the following equation:
Migration rate (%)=Y−X/X×100; X represents the certain weight of the PVC rigid tape; Y represents a weight of the PVC rigid tape losing a part of the plasticizer.

d. Test of Transparency:

The 0.4 mm sheet sample of Composition (A) was preheated at 185° C. for 3 minutes and heated at 185° C. for 3 minutes by a pressure apparatus, and was then cooled for 3 minutes to form a 4 mm sheet sample, which was detected for transparency by a gloss-haze meter (VGS-300A).

e. Test of Plastification Coefficient:

The 0.4 mm sheet sample of Composition (A) was formed into a 6 mm sheet sample by the same way as described in the test of transparency, which was put into contact with a durometer for 15 seconds to obtain a durometer value for calculating a plastification coefficient by the following equation in accordance with a hardness/PHR relation table.

Plastification coefficient=Sample amount/DOP amount f. Test of Tensile Strength:

The 0.4 mm sheet sample of Composition (A) was cut into a dumbbell shape and tested for tensile strength at a tensile speed of 200 mm/min by a universal test machine (Shimadzu AG-X Plus).

Example 1

According to the composition of Example 1 as shown in Table 1, 120 g of terephthalic acid (PTA), 310 g of 2-propylheptanol (2-EH), 0.168 g of 911 alcohol diluted with the 2-EH, and 0.6 g of tetraisopropyl titanate (TIPT) as a catalyst was used for a reaction. The mixture of the PTA, the 2-EH and the 911 alcohol and the catalyst were fed into a four-neck flask to carry out the reaction with the introduction of nitrogen gas, in which a reaction temperature is 225° C., a reaction time is 6 hours, and a reaction pressure is 5 mbar to 1033 mbar. The water generated in the reaction must be removed. When the reaction proceeds to an acid value of less than 1 mg KOH/g, a reaction mixture was neutralized with an alkali metal hydroxide containing aqueous solution to an acid value of less than 0.07 mg KOH/g. After that, a distillation process was performed to reduce an alcohol content to less than 300 ppm, and filtration and purification processes were performed to obtain a low migration di-2-ethylhexyl terephthalate for use as a plasticizer (i.e., a DOTP plasticizer).

The low migration di-2-ethylhexyl terephthalate was tested for basic and processing physical properties and the results were shown in Table 1, including a color number of 10 APHA, an acid value of 0.06 mg KOH/g, a purity of 99.8%, a migration rate of 2.73% based on an added amount of 80 PHR, a transparency of 89.5%, and a plastification coefficient of 1.05.

Example 2

The preparation method of Example 2 was the same as that of Example 1, but in the composition of Example 2 as shown in Table 1, 2-phenylphenol (2-PH) was used in place of 911 alcohol. A DOTP plasticizer is obtained under the same process conditions as those described in Example 1.

The DOTP plasticizer was tested for basic and processing physical properties and the results were shown in Table 1, including a color number of 12 APHA, an acid value of 0.06 mg KOH/g, a purity of 99.8%, a migration rate of 3.01% based on an added amount of 80 PHR, a transparency of 89.5%, and a plastification coefficient of 1.05.

Example 3

The preparation method of Example 3 was the same as that of Example 1, but in the composition of Example 3 as shown in Table 1, isobutanol was used in place of 911 alcohol. A DOTP plasticizer is obtained under the same process conditions as those described in Example 1.

The DOTP plasticizer was tested for basic and processing physical properties and the results were shown in Table 1, including a color number of 10 APHA, an acid value of 0.05 mg KOH/g, a purity of 99.6%, a migration rate of 3.22% based on an added amount of 80 PHR, a transparency of 89.4%, and a plastification coefficient of 1.047.

Example 4

The preparation method of Example 4 was the same as that of Example 1, but in the composition of Example 4 as shown in Table 1, a combination of 911 alcohol and isobutanol was used in place of 911 alcohol. A DOTP plasticizer is obtained under the same process conditions as those described in Example 1.

The DOTP plasticizer was tested for basic and processing physical properties and the results were shown in Table 1, including a color number of 10 APHA, an acid value of 0.06 mg KOH/g, a purity of 99.7%, a migration rate of 3.11% based on an added amount of 80 PHR, a transparency of 89.4%, and a plastification coefficient of 1.047.

Comparative Example 1

According to the composition of Comparative Example 1 as shown in Table 1, terephthalic acid, 2-propylheptanol (2-EH) and a catalyst were simultaneously fed into a four-neck flask to carry out a reaction with the introduction of nitrogen gas, in which a reaction temperature is 225° C., a reaction time is 6 hours, and a reaction pressure is 5 mbar to 1033 mbar. The water generated in the reaction must be removed. When the reaction proceeds to an acid value of less than 1 mg KOH/g, a reaction mixture was neutralized with an alkali metal hydroxide containing aqueous solution to an acid value of less than 0.07 mg KOH/g. After that, a distillation process was performed to reduce an alcohol content to less than 300 ppm, and filtration and purification processes were performed to obtain a di-2-ethylhexyl terephthalate (DOTP) plasticizer.

The DOTP plasticizer was tested for basic and processing physical properties and the results were shown in Table 1, including a color number of 10 APHA, an acid value of 0.06 mg KOH/g, a purity of 99.7%, a migration rate of 3.47% based on an added amount of 80 PHR, a transparency of 89.2%, and a plastification coefficient of 1.05.

Comparative Example 2

The preparation method of Comparative Example 2 was the same as that of Example 1, but in the composition of Example Comparative Example 2 as shown in Table 1, Diethyl glycol (DEG) was used in place of 911 alcohol. A DOTP plasticizer is obtained under the same process conditions as those described in Example 1.

The DOTP plasticizer was tested for basic and processing physical properties and the results were shown in Table 1, including a color number of 12 APHA, an acid value of 0.06 mg KOH/g, a purity of 99.8%, a migration rate of 3.43% based on an added amount of 80 PHR, a transparency of 89.4%, and a plastification coefficient of 1.06.

Results

1. In Examples 1 to 4, different alcohol components were respectively added in an esterification reaction between terephthalic acid (PTA) and 2-ethylhexanol (2-EH) to graft modify a resulting di-2-ethylhexyl terephthalate. Compared to an ungrafted DOTP plasticizer of Comparative Example 1, a modified DOTP plasticizer of Example 1 grafted with 911 alcohol (911A) had a significantly improved migration rate, being the best one at 2.73%.

2. In Example 4, 911 alcohol and isobutanol (IBA) were added together for graft modification and a resulting migration rate can reach up to 3.11%, which is better than the migration rate of 3.22% resulting from the graft modification in Example 3 where only isobutanol was added.

3. In Comparative Example 2, diethyl glycol (DEG) was added together for graft modification and a resulting migration rate is 3.43%, the improvement of which is less significant compared to the migration rate of Comparative Example 1.

4. The migration rates of Examples 1 to 4 are all better than the migration rates of Comparative Examples 1 and 2 under the premise that an added amount of the plasticizer reaches 80 PHR.

TABLE 1

Synthetic material compositions and basic and processing physical properties of Examples 1 to 4 and Comparative Examples 1 and 2

| | | Example number | | | | | |
|---|---|---|---|---|---|---|---|
| | | Examples | | | | Comparative Examples | |
| | Item | 1 | 2 | 3 | 4 | 1 | 2 |
| Synthetic material | PTA (g) | 120 | 120 | 120 | 120 | 120 | 120 |
| | 2-EH (g) | 310 | 310 | 310 | 310 | 310 | 310 |
| | 911A (g) | 0.168 | 0 | 0 | 0.168 | 0 | 0 |
| | 2-PH (g) | 0 | 0.175 | 0 | 0 | 0 | 0 |
| | IBA (g) | 0 | 0 | 0.078 | 0.039 | 0 | 0 |
| | DEG (g) | 0 | 0 | 0 | 0 | 0 | 0.1124 |
| | TIPT (g) | 0.6 | 0.6 | 0.6 | 0.6 | 0.6 | 0.6 |
| Basic physical properties | Acid value (mg KOH/g) | 0.06 | 0.06 | 0.05 | 0.06 | 0.06 | 0.06 |
| | Purity (%) | 99.8 | 99.8 | 99.6 | 99.7 | 99.7 | 99.8 |
| | APHA color number | 10 | 12 | 10 | 10 | 10 | 12 |
| Processing physical properties | Initial coloring degree | ◯ | ◯ | ◯ | ◯ | ◯ | ◯ |
| | Heat resistance | ⊚ | ⊚ | ⊚ | ⊚ | ◯ | ◯ |
| | Migration rate (%) based on an added amount of 80 PHR | 2.73 | 3.01 | 3.22 | 3.11 | 3.47 | 3.43 |
| | Tensile strength | 275 | 277 | 276 | 275 | 274 | 273 |
| | Transparency | 89.5 | 89.5 | 89.4 | 89.4 | 89.2 | 89.4 |
| | Plastification coefficient | 1.05 | 1.050 | 1.047 | 1.047 | 1.050 | 1.06 |

Note:
the ease of processability from "excellent" to "poor" are indicated in sequence by the symbols: ⊚ > ◯ > Δ;
PTA represents terephthalic acid;
2-EH represents 2-ethylhexanol;
911A represents 911 alcohol;
2-PH represents 2-propylheptanol;
IBA represents isobutanol;
DEG represents diethylene glycol;
TIPT represents tetraisopropyl titanate (catalyst).

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for preparing a plasticizer of modified di-2-ethylhexyl terephthalate, comprising performing a synthesis operation of adding isobutanol as a short chain alcohol component and 911 alcohol as a long chain alcohol component in an esterification reaction of terephthalic acid with 2-ethylhexanol, so as to obtain a crude ester product including the modified di-2-ethylhexyl terephthalate;

wherein the modified di-2-ethylhexyl terephthalate includes residues derived from the short chain alcohol component and the long chain alcohol component;

wherein the synthesis operation is carried out under a temperature from 30° C. to 225° C. and a pressure from 80 mbar to 1033 mbar.

2. The method according to claim 1, wherein in the esterification reaction, an amount of the 2-ethylhexanol is 2 to 5 times molar equivalence with respect to 1 molar equivalence of the terephthalic acid.

3. The method according to claim 2, wherein an added amount of the short chain alcohol component is from 0.1% to 0.5% of the molar equivalence of the terephthalic acid, and an added amount of the long chain alcohol component is from 0.1% to 0.5% of the molar equivalence of the terephthalic acid.

4. The method according to claim 1, wherein the esterification reaction is ended when an acid value is less than 0.07 mg KOH/g.

5. The method according to claim 1, further comprising performing a first dealcoholization operation of preliminarily reducing an alcohol content of the crude ester product under a temperature from 180° C. to 200° C. and a pressure from 80 mbar to 500 mbar.

6. The method according to claim 5, after the first dealcoholization operation, further comprising performing a second dealcoholization operation of further reducing the alcohol content of the crude ester product by gas stripping.

7. The method according to claim 1, wherein the esterification reaction is carried out in the presence of a catalyst that is a tin-based or titanium-based catalyst, and an added amount of the catalyst is from 0.2% to 1% of a total weight of the terephthalic acid.

8. The method according to claim 7, further comprising performing a filtration operation of filtering out at least the catalyst.

9. The method according to claim 1, wherein the modified di-2-ethylhexyl terephthalate has a molecular weight from 334 to 460, excluding the molecular weight of 390, a color number of less than 20 APHA, and a water content of less than 0.05%.

10. The method according to claim 1, wherein the modified di-2-ethylhexyl terephthalate has a structure represented by formula (1):

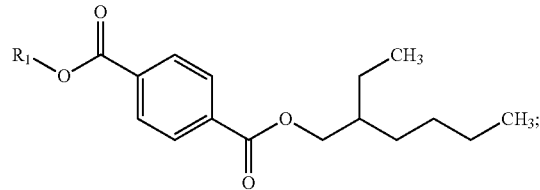

formula (1)

wherein R1 represents an alkyl group having 4, 9, 10 or 11 carbon atoms, excluding the alkyl group having 8 carbon atoms.

* * * * *